United States Patent [19]
Mougin et al.

[11] Patent Number: 5,851,517
[45] Date of Patent: Dec. 22, 1998

[54] COMPOSITION INCLUDING A DISPERSION OF POLYMER PARTICLES IN A NON-AQUEOUS MEDIUM

[75] Inventors: Nathalie Mougin, Paris; Jean Mondet, Aulney-Sous-Bois, both of France

[73] Assignee: L'Oreal, Paris, France

[21] Appl. No.: 793,266

[22] PCT Filed: Jun. 17, 1996

[86] PCT No.: PCT/FR96/00929

§ 371 Date: Feb. 21, 1997

§ 102(e) Date: Feb. 21, 1997

[87] PCT Pub. No.: WO97/00663

PCT Pub. Date: Jan. 9, 1997

[30] Foreign Application Priority Data

Jun. 21, 1995 [FR] France ................................. 95/07428

[51] Int. Cl.⁶ ................................ A61K 7/02; A61K 7/11
[52] U.S. Cl. .................. 424/78.02; 424/401; 424/78.03; 424/78.08; 514/937; 514/970
[58] Field of Search .............................. 424/78.02, 78.03, 424/78.08, 70.1, 70.11, 70.12, DIG. 2, 401; 514/772.3, 772.4, 772.6, 844, 937, 938, 944, 970

[56] References Cited

U.S. PATENT DOCUMENTS

| | | |
|---|---|---|
| 4,996,044 | 2/1991 | Mercado et al. . |
| 5,219,561 | 6/1993 | Gagnebien et al. . |
| 5,223,559 | 6/1993 | Arraudeau et al. . |
| 5,264,207 | 11/1993 | Bommelaer et al. . |
| 5,519,063 | 5/1996 | Mondet et al. ........................ 514/772.4 |
| 5,587,145 | 12/1996 | Lion et al. ................................. 424/45 |
| 5,643,581 | 7/1997 | Mougin et al. ......................... 424/401 |
| 5,660,820 | 8/1997 | Mondet et al. ....................... 424/70.16 |
| 5,747,013 | 5/1998 | Mougin et al. ......................... 424/707 |

FOREIGN PATENT DOCUMENTS

| | | |
|---|---|---|
| 0195575 | 9/1986 | European Pat. Off. . |
| 0409690 | 1/1991 | European Pat. Off. . |
| 0447286 | 9/1991 | European Pat. Off. . |
| 0486394 | 5/1992 | European Pat. Off. . |
| 0497144 | 8/1992 | European Pat. Off. . |
| 0502769 | 9/1992 | European Pat. Off. . |
| 78094041 | 11/1978 | Japan . |
| 61-12884 | 4/1986 | Japan . |
| 1202796 | 8/1970 | United Kingdom . |
| WO 95/09874 | 4/1995 | WIPO . |
| WO 96/10043 | 4/1996 | WIPO . |
| WO 96/10044 | 4/1996 | WIPO . |
| WO 97/00662 | 1/1997 | WIPO . |

*Primary Examiner*—Robert H. Harrison
*Attorney, Agent, or Firm*—Finnegan, Henderson Farabow, Garrett & Dunner, L.L.P.

[57] ABSTRACT

The invention relates to the use of a dispersion of surface-stabilized polymer particles in a non-aqueous medium, in a cosmetic, hygiene or pharmaceutical composition. Moreover, the invention also relates to compositions comprising the above-mentioned dispersion of polymer particles.

22 Claims, No Drawings

COMPOSITION INCLUDING A DISPERSION OF POLYMER PARTICLES IN A NON-AQUEOUS MEDIUM

This application is a 371 of PCT/FR96/00929, filed Jun. 17, 1996.

The present invention relates to a cosmetic, pharmaceutical or hygiene composition comprising a dispersion of polymer particles dispersed in a non-aqueous medium, as well as to the use of such a dispersion in a cosmetic, pharmaceutical or hygiene composition.

It is known to use in cosmetics certain dispersions of polymer particles of nanometric size in organic media such as lower alcohols or aromatic or aliphatic hydrocarbons. The polymers are, in this case, usually used as film-forming agent in make-up products such as mascaras, eye-liners, eyeshadows or nail varnishes. The cosmetic compositions obtained after incorporation of these dispersions of polymer particles are not always of satisfactory stability. Make-up compositions based on an organic polymer dispersion in a medium consisting of lower monoalcohols or aliphatic or aromatic hydrocarbons are also known in patent application JP-A-78 94041. Dispersions of acrylic polymers in an alcoholic medium which are stabilized with a block copolymer based on polymethyl methacrylate and poly-tert-butyl acrylate are also known in application WO-A-95/09074.

The Applicant has discovered, surprisingly, novel dispersions of polymer particles stabilized by specific stabilizers, which will be defined later, in many types of non-aqueous medium. The aim of the present invention is to propose a dispersion of particles which remain in the form of elementary particles, without forming agglomerates, when they are in dispersion in non-aqueous media.

One subject of the present invention is thus a composition comprising, in a cosmetically, pharmaceutically and/or hygienically acceptable medium, a dispersion of particles of at least one polymer stabilized at the surface by a stabilizer in a non-aqueous medium, characterized in that:

A) the non-aqueous medium consists of at least one non-aqueous liquid compound chosen from the group consisting of:
non-aqueous liquid compounds having a global solubility parameter, according to the Hansen solubility space, of less than 17 $(MPa)^{1/2}$,
or monoalcohols having a global solubility parameter, according to the Hansen solubility space, of less than or equal to 20 $(MPa)^{1/2}$,
or mixtures thereof, and B)
(i) when the non-aqueous medium comprises at least one silicone oil, the stabilizer is chosen from the group consisting of sequential or grafted block copolymers comprising at least one block of polyorganosiloxane type and at least one block of a radical polymer or of a polyether or of a polyester,
(ii) when the non-aqueous medium does not comprise a silicone oil, the stabilizer is chosen from the group consisting of:
(a) sequential or grafted block copolymers comprising at least one block of polyorganosiloxane type and at least one block of a radical polymer or of a polyether or of a polyester,
(b) copolymers of acrylates or methacrylates of $C_1$–$C_4$ alcohols, and of acrylates or methacrylates of $C_8$–$C_{30}$ alcohols,
(c) sequential or grafted block copolymers comprising at least one block resulting from the polymerization of dienes, which is hydrogenated or non-hydrogenated, and at least one block of a vinyl or acrylic polymer or of a polyether or of a polyester, or mixtures thereof.

Another subject of the invention is the use of the said particle dispersion in and for the preparation of a cosmetic, hygiene or pharmaceutical composition.

One advantage of the present invention is that it is thus possible to calibrate at will the size of the polymer particles, as well as to modify their size polydispersity during the synthesis. This is not possible when pigments in particulate form are used, since their constitution does not allow the average size of the particles to be modified, nor their hardness.

Another advantage of the invention is that it is thus possible to obtain polymer particles of very small size, in particular of nanometric size, which is not the case, for example, with other types of particles such as microspheres whose diameter is generally greater than 1 micron. This large size, of the order of a micron, has the drawback of entailing a certain visibility of the particles with the eye, when they are in a composition and/or when they are applied to the skin, as well as poor stability of the composition comprising the said dispersion.

Thus, another advantage of the use of the dispersion according to the invention is to allow the production of a stable composition, which may be transparent, translucent or opaque, according to the size of the polymer particles which are dispersed therein.

The dispersions according to the invention thus consist of particles, generally spherical particles, of at least one surface-stabilized polymer in a non-aqueous medium.

These dispersions may, in particular, be in the form of nanoparticles of polymers in stable dispersion in a non-aqueous medium. The nanoparticles are preferably between 5 and 600 nm in size, given that beyond about 600 nm, the particle dispersions become much less stable.

The polymers used in the present application may be of any nature. It is thus possible to employ radical polymers, polycondensates or even polymers of natural origin. The polymer may be chosen by a person skilled in the art on the basis of its properties, depending on the desired subsequent use for the composition. These polymers may, in particular, be crosslinked.

Thus, it is possible to use film-forming polymers, preferably having a low glass transition temperature (Tg), which is less than or equal to room temperature. A dispersion is thus obtained which can form a film when it is applied onto a support-substrate, which is not the case when dispersions of inorganic pigments according to the prior art are used.

It is also possible to use non-film-forming polymers, which are optionally crosslinked, which may be used as fillers dispersed stably in the non-aqueous medium. This use also constitutes a subject of the invention.

The polymers which can be used in the context of the present invention preferably have a number-average molecular weight of about from 2000 to 10,000,000, and a glass transition temperature of from −100° C. to 300° C.

Among the non-crosslinked film-forming polymers which may be mentioned are acrylic or vinyl radical copolymers or homopolymers, preferably having a Tg less than or equal to 30° C.

It is possible to add a plasticizer to the polymer dispersion so as to lower the Tg of the polymers used. The plasticizer may be chosen from the plasticizers usually used in the field of application and, in particular, from compounds liable to be solvents for the polymer.

Among the non-film-forming polymers which may be mentioned are vinyl or acrylic radical copolymers or homopolymers, which are optionally crosslinked, preferably having a Tg of greater than or equal to 40° C., such as polymethyl methacrylate, polystyrene or poly-tert-butyl acrylate.

The liquid compounds of the non-aqueous medium of the polymer dispersion must be liquid at room temperature.

The global solubility parameter δ, which is global according to the Hansen solubility space, is defined in the article "Solubility parameter values" by Eric A. Grulke in the publication "Polymer Handbook" 3rd Edition, chapter VII, pages 519–559, by the relationship:

$$\delta = (d_D^2 + d_P^2 + d_H^2)^{1/2}$$

in which $d_D$ characterizes the London dispersion forces arising from the formation of dipoles induced during molecular collisions, $d_P$ characterizes the Debye forces of interaction between permanent dipoles, $d_H$ characterizes the specific forces of interaction (of the hydrogen bonding, acid/base, donor/acceptor, etc. type).

The definition of the solvents in the three-dimensional solubility space according to Hansen is described in the article by C. M. Hansen: "The three dimensional solubility parameters" J. Paint Technol. 39, 105 (1967).

Among the non-aqueous liquid compounds having a global solubility parameter according to the Hansen solubility space of less than or equal to 17 $(MPa)^{1/2}$ which may be mentioned are liquid fats, in particular oils, which may be chosen from natural or synthetic, carbon-based, hydrocarbon, fluoro and/or silicone oils, which are optionally branched, alone or as a mixture.

Among these oils which may be mentioned are plant oils formed by fatty acid esters of polyols, in particular triglycerides, such as sunflower oil, sesame oil or rapeseed oil, or esters derived from acids or alcohols with a long chain (that is to say having from 6 to 20 carbon atoms), in particular esters of formula RCOOR' in which R represents a higher fatty acid residue containing from 7 to 19 carbon atoms and R' represents a hydrocarbon chain containing from 3 to 20 carbon atoms, such as palmitates, adipates and benzoates, in particular diisopropyl adipate. Mention may also be made of hydrocarbons and, in particular, liquid paraffin, liquid petrolatum, or hydrogenated polyisobutylene, isododecane or alternatively "ISOPARs", volatile isoparaffins.

Mention may also be made of silicone oils such as polydimethylsiloxanes and polymethylphenylsiloxanes, which are optionally substituted with aliphatic and/or aromatic groups, which are optionally fluorinated, or with functional groups such as hydroxyl, thiol and/or amine groups, and volatile silicone oils, in particular cyclic ones.

It is also possible to use a non-aqueous medium consisting of a single solvent or of a solvent mixture, chosen from:

linear, branched or cyclic esters having more than 6 carbon atoms, ethers having more than 6 carbon atoms, ketones having more than 6 carbon atoms.

The expression monoalcohols having a global solubility parameter according to the Hansen solubility space of less than or equal to 20 $(MPa)^{1/2}$ is understood to refer to aliphatic fatty monoalcohols having at least 6 carbon atoms, the hydrocarbon chain containing no substitution group.

Monoalcohols according to the invention which may be mentioned are oleyl alcohol, decanol, dodecanol, octadecanol and linoleyl alcohol.

The choice of the non-aqueous medium is made by a person skilled in the art on the basis of the nature of the monomers constituting the polymer and/or the nature of the stabilizer, as indicated below.

In general, the dispersion according to the invention may be prepared in the following way, given by way of example.

The polymerization may be carried out in dispersion, that is to say by precipitation of the polymer which is being formed, with protection of the articles formed with a stabilizer.

A mixture is thus prepared comprising the initial monomers as well as a radical initiator. This mixture is dissolved in a solvent which is referred to in the rest of the present description as the "synthesis solvent".

When the non-aqueous medium chosen is a non-volatile silicone oil or hydrocarbon oil, the polymerization may be carried out in an apolar organic solvent (synthesis solvent), followed by addition of the hydrocarbon oil (which must be miscible with the said synthesis solvent) and selective distillation of the synthesis solvent.

A synthesis solvent is thus chosen such that the initial monomers and the radical initiator are soluble therein and the polymer particles obtained are insoluble therein, so that they precipitate therein when they are formed.

In particular, the synthesis solvent may be chosen from alkanes such as heptane or cyclohexane.

When the non-aqueous medium chosen is a volatile hydrocarbon oil, the polymerization may be carried out directly in the said oil which thus also acts as synthesis solvent. The monomers must also be soluble therein, as well as the radical initiator, and the polymer obtained must be insoluble therein.

The monomers are preferably present in the synthesis solvent, before polymerization, in a proportion of 5–20 % by weight. The monomers may all be present in the solvent before the start of the reaction, or part of the monomers may be added as the polymerization reaction proceeds.

The radical initiator may in particular be azobisisobutyronitrile or 2-tert-butylperoxyethyl hexanoate.

The polymer particles are surface-stabilized, when they are formed during the polymerization, by means of the stabilizer.

The stabilization may be effected by any known means, and in particular by direct addition of the stabilizer during the polymerization.

The stabilizer is preferably also present in the mixture before polymerization. However, it is also possible to add it continuously, in particular when the monomers are also added continuously.

2–30% by weight of stabilizer may be used relative to the initial monomer mixture, and preferably 5–20% by weight.

As sequential or grafted block copolymers comprising at least one block of polyorganosiloxane type and at least one block of a radical polymer, mention may be made of grafted copolymers of acrylic/silicone type which may be employed in particular when the non-aqueous medium contains silicone.

As sequential or grafted block copolymers comprising at least one block of polyorganosiloxane type and at least one polyether, dimethicone copolyols such as those sold under the name "Dow Corning 3225C" by the company Dow Corning and lauryl methicones such as those sold under the name "Dow Corning Q2-5200" by the company Dow Corning may be used.

As copolymers of acrylates or methacrylates of $C_1$–$C_4$ alcohols and of acrylates or methacrylates of $C_8$–$C_{30}$ alcohols, the stearyl methacrylate/methyl methacrylate copolymer may be used.

As sequential or grafted block copolymers comprising at least one block resulting from the polymerization of dienes, which is hydrogenated or non-hydrogenated, and at least one block of a vinyl polymer, mention may be made of sequential copolymers, in particular of "diblock" or "triblock" type of the polystyrene/polyisoprene or polystyrene/ polybutadiene type such as those sold under the name "Luvitol HSB" by BASF, of the polystyrene/copoly (ethylene-propylene) type such as those sold under the name "Kraton" by Shell Chemical Co. or alternatively of the polystyrene/copoly(ethylene-butylene) type.

As sequential or grafted block copolymers comprising at least one block resulting from the polymerization of dienes, which is hydrogenated or non-hydrogenated, and at least one block of an acrylic polymer, mention may be made of di- or trisequential poly(methyl methacrylate)/polyisobutylene copolymers or grafted copolymers containing a poly(methyl methacrylate) skeleton and containing polyisobutylene grafts.

As sequential or grafted block copolymers comprising at least one block resulting from the polymerization of dienes, which is hydrogenated or non-hydrogenated, and at least one block of a polyether, mention may be made of di- or trisequential polyoxyethylene/polybutadiene or polyoxyethylene/polyisobutylene copolymers.

When a random polymer is used as stabilizer, it is chosen such that it possesses a sufficient amount of groups which make it soluble in the synthesis solvent envisaged.

The dispersions obtained according to the invention may then be used in a composition, in particular a cosmetic, pharmaceutical and/or hygiene composition, such as a composition to care for or make up the skin or keratin substances, or alternatively a hair composition or a sun composition.

Depending on the application, it may be chosen to use film-forming or non-film-forming polymer dispersions, in volatile or non-volatile oils.

The composition may then contain, depending on the application envisaged, the usual constituents for this type of composition.

Among these constituents which may be mentioned are fatty substances, and in particular waxes and oils, gums and/or pasty fatty substances, which are hydrocarbon-based and/or silicone-based, and pulverulent compounds such as pigments, fillers and/or pearlescent agents.

Among the waxes which may be present in the composition according to the invention, mention may be made, alone or as a mixture, of hydrocarbon waxes such as beeswax; carnauba wax, candelilla wax, ouricurry wax, Japan wax, cork fibre wax or sugar cane wax; paraffin wax, lignite wax; microcrystalline waxes; lanolin wax; montan wax; ozokerites; polyethylene waxes; the waxes obtained by Fischer-Tropsch synthesis; hydrogenated oils, fatty esters and glycerides which are solid at 25° C. It is also possible to use silicone waxes, among which mention may be made of polymethylsiloxane alkyls, alkoxys and/or esters.

Among the oils which may be present in the composition according to the invention, mention may be made, alone or as a mixture, of hydrocarbon oils such as liquid paraffin or liquid petrolatum; perhydrosqualene; arara oil; sweet almond oil, calophyllum oil, palm oil, castor oil, avocado oil, jojoba oil, olive oil or cereal germ oil; esters of lanolic acid, of oleic acid, of lauric acid or of stearic acid; alcohols such as oleyl alcohol, linoleyl alcohol or linolenyl alcohol, isostearyl alcohol or octyldodecanol. Mention may also be made of silicone oils such as PDMSs, which are optionally phenylated, such as phenyltrimethicones. It is also possible to use volatile oils such as cyclotetradimethylsiloxane, cyclopentadimethylsiloxane, cyclohexadimethylsiloxane, methylhexyldimethylsiloxane, hexamethyldisiloxane or isoparaffins.

The pigments may be white or coloured and inorganic and/or organic. Among the inorganic pigments which may be mentioned are titanium dioxide, zirconium dioxide and cerium dioxide, as well as zinc oxide, iron oxide, chromium oxide and ferric blue. Among the organic pigments which may be mentioned are carbon black and barium, strontium, calcium or aluminium lakes.

The pearlescent agents may be chosen from mica coated with titanium oxide, with iron oxide, with natural pigment or with bismuth oxychloride, and coloured titanium mica.

The fillers may be inorganic or synthetic and lamellar or non-lamellar. Mention may be made of talc, mica, silica, kaolin, nylon powder, polyethylene powder, Teflon, starch, titanium mica, natural mother-of-pearl, boron nitride, hollow microspheres such as Expancel (Nobel Industry), polytrap (Dow Corning) and silicone resin microbeads (Tospearls from Toshiba, for example).

The composition may also comprise any additive usually used in the cosmetic field, such as antioxidants, fragrances, essential oils, preserving agents, cosmetic active agents, moisturizers, vitamins, essential fatty acids, sphingoceryls, sunscreens, surfactants, liposoluble polymers such as polyalkylenes, in particular polybutene, polyacrylates and silicone polymers which are compatible with fatty substances. Obviously, a person skilled in the art will take care to select this or these possible additional compounds, and/or the amount thereof, such that the advantageous properties of the composition according to the invention are not, or are substantially not, adversely affected by the addition envisaged.

The compositions according to the invention may be in any acceptable form which is common for a cosmetic, hygiene or pharmaceutical composition.

In particular, the composition according to the invention may be in the form of an oil-in-water or water-in-oil emulsion, a lotion, a foam or a spray.

Among the applications preferably intended by the present invention, mention may be made more particularly of:

the field of hair products (washing, care or beauty of the hair), the compositions according to the invention being in particular in the form of aerosols, foams, shampoos, conditioners, lotions or gels for styling or treating, or lacquers or lotions for setting, shaping or fixing the hair. In this case, the hair composition preferably comprises a crosslinked polymer dispersion in a silicone oil.

the field of make-up products, in particular for making up the eyelashes, the compositions being in the form of mascara or eye-liner; lipstick or lip gloss or foundation.

The invention is illustrated in greater detail in the examples which follow.

EXAMPLE 1

360 g of n-heptane and 15 g of sequential stabilizing polymer of polystyrene/copoly(ethylene-propylene) diblock copolymer type sold under the name Kraton G1701 (Shell) are mixed together.

The mixture is heated for at least 3 h, at about 60° C., in order to obtain a dispersed solution.

At 25° C., 19 g of methyl methacrylate, 1 g of ethylene glycol dimethacrylate, 0.4 g of 2-tert-butylperoxyethyl hexanoate (Trigonox 21S from Akzo) and 5 g of heptane are added to the mixture.

The mixture is heated at 75° C., under nitrogen, for at least 3 hours.

A mixture of 76 g of methyl methacrylate, 4 g particles in a non-aqueous medium of ethylene glycol dimethacrylate, 1.6 g of 2-tert-butylperoxyethyl hexanoate (Trigonox 21S from Akzo) and 80 g of heptane is then added at 75° C. and over 1.5 hours.

At the end of the addition, the mixture is heated at 85° C. for 4 hours, 1 g of Trigonox dissolved in 5 g of heptane is added and the mixture is heated for a further 7 hours at 85° C.

A stable dispersion of milky appearance is obtained, with a solids content of 18.6% by weight.

The particle size, measured by quasi-elastic light scattering with a Coulter N4 SD machine, gives the following results:

average particle size: 160 nm polydispersity: less than 0.1.

50 g of the dispersion are mixed in the above heptane with 28.5 g of non-volatile liquid paraffin. The heptane is selectively evaporated off using a rotary evaporator.

A stable dispersion of milky appearance is thus obtained, having a solids content of 25% by weight, of polymethyl methacrylate crosslinked with ethylene glycol dimethacrylate, in a liquid paraffin.

EXAMPLE 2

A dispersion of polymethyl methacrylate crosslinked with ethylene glycol dimethacrylate, in a branched and volatile liquid paraffin (Isopar L from Exxon) is prepared according to the method of Example 1, replacing the heptane by the said liquid paraffin Isopar L.

A stable dispersion is thus obtained, having a solids content of 19% by weight and an average particle size of 159 nm (polydispersity: 0.05).

EXAMPLE 3

20 g of the dispersion are mixed in the above Isopar with 16.2 g of cyclotetradimethylsiloxane (volatile silicone oil).

A stable dispersion of milky appearance is thus obtained, consisting of 3.8 g of polymethyl methacrylate crosslinked with ethylene glycol dimethacrylate, 16.2 g of volatile liquid paraffin and 16.2 g of volatile silicone oil.

EXAMPLE 4

20 g of the dispersion are mixed in the Isopar of Example 2 with 16.2 g of $C_{12}$–$C_{15}$ alkyl benzoate (Finsolv TN from Witco).

A stable dispersion of milky appearance is thus obtained, consisting of 3.8 g of polymethyl methacrylate crosslinked with ethylene glycol dimethacrylate, 16.2 g of volatile liquid paraffin and 16.2 g of non-volatile ester.

EXAMPLE 5

360 g of n-heptane and 15 g of sequential stabilizing polymer of polystyrene/copoly (ethylene-propylene) diblock copolymer type sold under the name Kraton G1701 (Shell) are mixed together.

The mixture is heated for at least 3 h, at about 60° C., in order to obtain a dispersed solution.

At 25° C., 20 g of methyl methacrylate, 0.4 g of 2-tert-butylperoxyethyl hexanoate and 5 g of heptane are added to the mixture.

The mixture is heated at 75° C., under nitrogen, for at least 3 hours. A mixture of 80 g of methyl acrylate, 1.6 g of 2-tert-butylperoxyethyl hexanoate and 80 g of heptane is then added at 75° C. and over 1.5 hours.

At the end of the addition, the mixture is heated at 85° C. for 4 hours, 1 g of Trigonox dissolved in 5 g of heptane is added and the mixture is heated for a further 7 hours at 85° C.

A stable dispersion of milky appearance is obtained, with a solids content of 19% by weight.

The particle size, measured by quasi-elastic light scattering with a Coulter N4 SD machine, gives the following results:

average particle size: 230 nm polydispersity: less than 0.1.

50 g of the dispersion are mixed in the above heptane with 28.5 g of non-volatile liquid paraffin. The heptane is selectively evaporated off using a rotary evaporator.

A stable dispersion of milky appearance is thus obtained, having a solids content of 25% by weight, of polymethyl acrylate (Tg=10° C.) in a non-volatile liquid paraffin.

EXAMPLE 6

A dispersion of polymethyl acrylate in a branched and volatile liquid paraffin (Isopar L from Exxon) is prepared in the same way as in Example 5, replacing the heptane by the said liquid paraffin Isopar L.

A stable dispersion is thus obtained, having a solids content of 20% by weight and an average particle size of 197 nm (polydispersity: 0.06).

This dispersion is film-forming and gives, after drying, a continuous and transparent film.

EXAMPLE 7

360 g of isododecane and 15 g of sequential stabilizing polymer of polystyrene/copoly (ethylene-propylene) diblock copolymer type sold under the name Kraton G1701 (Shell) are mixed together.

The mixture is heated for at least 3 h, at about 60° C., in order to obtain a dispersed solution.

At 25° C., 48 g of methyl acrylate, 5 g of butyl acrylate, 3 g of acrylic acid, 0.4 g of 2-tert-butylperoxyethyl hexanoate (Trigonox 21S from Akzo) and 5 g of isododecane are added to the mixture.

The mixture is heated at 75° C., under nitrogen, for at least 3 hours.

A mixture of 48 g of methyl acrylate, 20 g of butyl acrylate, 12 g of acrylic acid, 1.6 g of Trigonox 21S and 80 g of isododecane is then added at 75° C. and over 1.5 hours.

At the end of the addition, the mixture is heated at 85° C. for 4 hours, 1 g of Trigonox 21S dissolved in 5 g of isododecane is added and the mixture is heated for a further 7 hours at 85° C.

A stable dispersion is obtained, with a solids content of 20.5% by weight.

The particle size, measured by quasi-elastic light scattering with a Coulter N4 SD machine, gives the following results:

average particle size: 175 nm polydispersity: less than 0.1.

3.2 g of 2-amino-2-methylpropanol were added to 100 g of the dispersion thus obtained and the mixture was then stirred for 1 hour. 2.7 g of glycerol were then added and the mixture was then stirred for 5 h.

A stable and homogeneous dispersion was obtained. The dispersion medium is clear, thus showing that the glycerol was incorporated into the polymer particles.

EXAMPLE 8

255 g of n-heptane and 150 g of dimethicone copolyol sold under the name Dow Corning 3225 C by the company Dow Corning (silicone stabilizer) were mixed together.

The mixture was heated at 60° C. and 19 g of methyl methacrylate, 1 g of acrylic acid, 0.4 g of 2-tert-butylperoxyethyl hexanoate (Trigonox 21S from Akzo) and 10 g of heptane were then added.

The mixture was heated at 75° C., under nitrogen, for 3 h. A mixture of 76 g of methyl methacrylate, 4 g of methacrylic acid, 1.6 g of Trigonox 21S and 50 g of heptane was then added, at 75° C., over 1 h 30. The mixture was left to react for 8 h at 75° C.

A stable dispersion with a milky appearance was thus obtained, having a solids content of 17.7%.

The particle size, measured by quasi-elastic light scattering with a Coulter N4 SD machine, gives the following results:

average particle size: 360 nm polydispersity: less than 0.1.

50 g of the dispersion obtained were then mixed with 30 g of dimethylcyclopentasiloxane and the heptane was then selectively evaporated off. A stable dispersion was thus obtained.

EXAMPLE 9

A polymer dispersion similar to that of Example 8 was prepared, replacing the starting mixture by a mixture consisting of 130 g of heptane and 17.7 g of lauryl methicone copolyol sold under the name "Dow Corning 5200" by the company Dow Corning, as stabilizer.

A stable particle dispersion was thus obtained.

The particle size, measured by quasi-elastic light scattering with a Coulter N4 SD machine, gives the following results:

average particle size: 350 nm polydispersity: less than 0.1.

EXAMPLE 10

Anti-wrinkle Cream

An oil-in-water emulsion having the following composition was prepared:

| Oily phase | |
|---|---|
| Sorbitan tristearate | 0.9 g |
| Glyceryl monostearate | 3.0 g |
| Apricot oil | 2.0 g |
| Hydrogenated polyisobutylene | 4.0 g |
| Polyethylene glycol stearate containing 40 mol of ethylene oxide | 2.0 g |
| Dispersion of Example 2 | 7.0 g |
| Aqueous phase | |
| Polyacrylamide in reverse emulsion containing 40% AM (Sepigel 305 from the company Seppic) | 0.9 g |
| Sequestering agent | 0.05 g |
| Preserving agent | 0.5 g |
| Glycerol | 3.0 g |
| Water qs | 100 g |

The oily phase was dispersed in the aqueous phase with stirring using a homogenizer. An oil-in-water emulsion was thus obtained, which is used as an anti-wrinkle cream.

EXAMPLE 11

An emulsion having the following composition is prepared:

| Oily phase | |
|---|---|
| Diglyceryl diisostearate | 2.0 g |
| Laurylmethicone copolyol (Dow Corning Q2-5200) | 2.0 g |
| Liquid petrolatum | 1.0 g |
| Cyclomethicone | 21 g |
| Dispersion of Example 1 | 4.0 g |
| Aqueous phase | |
| Magnesium sulphate | 1.0 g |
| Methylparaben | 0.25 g |
| Chlorphenesin | 0.3 g |
| Water qs | 100 g |

The process is carried out in the same way as in Example 1.

EXAMPLE 12

Water-in-oil Emulsion

An emulsion having the following composition is prepared:

| Phase A | |
|---|---|
| Stearic acid | 0.4 g |
| Polyethylene glycol stearate containing 40 mol of ethylene oxide | 3.5 g |
| Cetyl alcohol | 3.2 g |
| Mixture of glyceryl mono-, di- and tristearate | 3.0 g |
| Myristyl myristate | 2.0 g |
| Isopropyl myristate | 7.0 g |
| Dispersion of Example 5 | 8.0 g |
| Phase B | |
| Cyclopentadimethylsiloxane | 5.0 g |
| Phase C | |
| Glycerol | 3.0 g |
| Preserving agent | 0.2 g |
| Water qs | 100 g |

The constituents of phase A are dissolved at 80° C. When the mixture is clear, the temperature is lowered to 65° C. and phase B is added. The temperature is maintained at 65° C.

The constituents of phase C are dissolved at 85° C.–90° C. and the temperature is then brought to 65° C. The mixture of phases A and B is poured into phase C and the resulting mixture is cooled with stirring to room temperature.

A white care cream for daily protection of the skin against the harmful effects of UV radiation and to prevent the formation of wrinkles and fine lines is obtained.

EXAMPLE 13

A facial gel having the following composition is prepared:

| | |
|---|---|
| Isopropyl palmitate | 10 g |
| Petrolatum (wax) | 5 g |
| Modified hectorite (clay) | 0.15 g |
| Ozokerite (clay) | 5 g |
| Oxyethylenated sorbitan septaoleate (40 EO) | 5 g |
| Dispersion of Example 6 (25% solids content) | 75 g |

A gel having good cosmetic properties is obtained.

EXAMPLE 14

A care oil having the following composition is prepared:

| | |
|---|---|
| Dispersion of Example 4 | 70 g |
| Jojoba oil | 15 g |
| Soya oil | 15 g |

A care oil which may be applied to the body or face is obtained.

EXAMPLE 15

A hair fixing composition was prepared according to the following procedure:

50 g of the dispersion of Example 5 and 7.5 g of non-volatile liquid paraffin were added to 50 g of the dispersion obtained in Example 1.

This mixture was introduced into a pump-dispenser bottle.

The product was sprayed in the form of droplets onto the hair. After drying, the product displays good adhesion to the hair and gives rise to rigid fixing which provides the hairstyle with hold.

The product is readily removed by brushing.

We claim:

1. A composition comprising, in a cosmetically, pharmaceutically and/or hygienically acceptable medium,
    a dispersion of surface-stabilized polymeric particle in a non-aqueous medium, wherein said particles
        are particles of at least one polymer formed from monomers and
        are stabilized at their surface by at least one stabilizer
    wherein
    a) said non-aqueous medium comprises at least one non-aqueous liquid compound wherein said non-aqueous liquid compound is:
        a non-aqueous liquid compound having a global solubility parameter, according to the Hansen solubility space, of less than 17 $(MPa)^{1/2}$, and
        a monoalcohol having a global solubility parameter, according to the Hansen solubility space, of less than or equal to 20 $(MPa)^{1/2}$,
        or a mixture thereof,
    and
    b) (i) when said non-aqueous medium comprises at least one non-aqueous liquid compound which is a silicone oil, said at least one stabilizer is a sequential or grafted block copolymer, or a mixture thereof, comprising at least one block of polyorganosiloxane structure and at least one block of a radical polymer or of a polyether or of a polyester, and
    (ii) when said non-aqueous medium comprises at least one non-aqueous liquid compound which is not a silicone oil, said at least one stabilizer is:
        (A) a sequential or grafted block copolymers, or a mixture thereof, comprising at least one block of polyorganosiloxane structure and at least one block of a radical polymer or of a polyether or of a polyester,
        (B) a copolymer of acrylates or methacrylates of $C_1$–$C_4$ alcohols, or of acrylates or methacrylates of $C_8$–$C_{30}$ alcohols,
        (C) a sequential or grafted block copolymer, or a mixture thereof, comprising at least one block resulting from the polymerization of dienes, which is optionally hydrogenated, and at least one block of at least one polymer wherein said at least one polymer is a vinyl or acrylic polymer, polyether, or polyester; or a mixture thereof.

2. A composition according to claim 1, wherein said surface-stabilized polymer particles are spherical particles and have an average diameter ranging from 5 to 600 nm.

3. A composition according to claim 1, wherein said at least one polymer is a radical polymer, polycondensate, or polymer of natural origin, or a mixture thereof.

4. A composition according to claim 1, wherein said at least one polymer is crosslinked.

5. A composition according to claim 1, wherein said at least one polymer is an acrylic or vinyl copolymer or homopolymer, which is optionally crosslinked, or a mixture thereof.

6. A composition according to claim 1, wherein said at least one polymer is polymethyl methacrylate, polystyrene or poly-tert-butyl acrylate.

7. A composition according to claim 1, wherein said dispersion further comprises at least one plasticizer.

8. A composition according to claim 1, wherein said monoalcohol having a global solubility parameter of less than or equal to 20 $(MPa)^{1/2}$ is a monoalcohol formed by a fatty aliphatic monoalcohol having at least 6 carbon atoms.

9. A composition according to claim 1, wherein said at least one non-aqueous liquid compound having a global solubility parameter of less than 17 $(MPa)^{1/2}$ is a natural or synthetic carbon-based, hydrocarbon, fluoro or silicone oil, or a mixture thereof.

10. A composition according to claim 1, wherein said non-aqueous liquid compounds having a global solubility parameter of less than 17 $(MPa)^{1/2}$ is a linear, branched or cyclic ester having more than 6 carbon atoms, ether having more than 6 carbon atoms, or ketone having more than 6 carbon atoms, or a mixture thereof.

11. A composition according to claim 1, wherein said at least one stabilizer is a sequential block copolymer comprising at least one block resulting from the polymerization of dienes and is a polystyrene/polyisoprene, polystyrene/polybutadiene, polystyrene/copoly(ethylene-propylene) or polystyrene/copoly(ethylene-butylene) sequential copolymer, or a mixture thereof.

12. A composition according to claim 1, wherein said at least one stabilizer is a grafted block polymer comprising at least one block of polyorganosiloxane structure and at least one block of a radical polymer and is a grafted acrylic/silicone copolymer.

13. A composition according to claim 1, wherein said at least one stabilizer is a grafted block polymer comprising at least one block of polyorganosiloxane structure and at least one block of a polyether and is a dimethicone copolyol or a lauryl dimethicone, or a mixture thereof.

14. A composition according to claim 1, wherein said at least one stabilizer is a sequential or grafted block copolymer comprising at least one block resulting from the polymerization of dienes and at least one block of an acrylic polymer and is a poly(methyl methacrylate)/polyisobutylene di- or trisequential copolymer or a grafted copolymer containing a poly(methyl methacrylate) skeleton and containing polyisobutylene grafts, or a mixture thereof.

15. A composition according to claim 1, wherein said at least one stabilizer is a sequential or grafted block copolymer comprising at least one block resulting from the polymerization of dienes and at least one block of a polyether and is a polyoxyethylene/polybutadiene or polyoxyethylene/polyisobutylene di- or trisequential copolymer, or a mixture thereof.

16. A composition according to claim 1, wherein said at least one stabilizer is present in said dispersion in a proportion ranging from 2–30% by weight of stabilizer relative to said monomers which form said at least one polymer.

17. A composition according to claim 16, wherein said at least one stabilizer is present in said dispersion in a proportion ranging from 5–20% by weight of stabilizer relative to said monomers.

18. A composition according to claim 1, further comprising at least one hydrocarbon-based or silicone-based fatty substance wherein said fatty substance is a wax, oil, gum, pasty fatty substance, or a mixture thereof.

19. A composition according to claim 1, further comprising at least one additional component wherein said additional component is a pigment, filler, pearlescent agent, or a mixture thereof.

20. A composition according to claim 1, wherein said composition is in the form of a composition for caring for or making up the skin or keratinous substances, a hair composition or a sun-screen composition.

21. A method of preparing a cosmetic, hygiene or pharmaceutical composition, comprising the step of including in said composition at least one dispersion of surface-stabilized polymeric particles in a non-aqueous medium, wherein said particles are particles of at least one polymer formed from monomers and are stabilized at their surface by at least one stabilizer, and further wherein a) said non-aqueous medium comprises at least one non-aqueous liquid compound wherein said non-aqueous liquid compound is:
   a non-aqueous liquid compound having a global solubility parameter, according to the Hansen solubility space, of less than 17 $(MPa)^{1/2}$,
   or a monoalcohol having a global solubility parameter, according to the Hansen solubility space, of less than or equal to 20 $(MPa)^{1/2}$,
   or a mixture thereof,
and
b) (i) when said non-aqueous medium comprises at least one non-aqueous liquid compound which is a silicone oil, said at least one stabilizer is a sequential or grafted block copolymer, or a mixture thereof, comprising at least one block of polyorganosiloxane structure and at least one block of a radical polymer or of a polyether or of a polyester,
   (ii) when said non-aqueous medium comprises at least one non-aqueous liquid compound which is not a silicone oil, said at least one stabilizer is:
   (A) a sequential or grafted block copolymer, or a mixture thereof comprising at least one block of polyorganosiloxane structure and at least one block of a radical polymer or of a polyether or of a polyester,
   (B) a copolymer of acrylates or methacrylates of $C_1$–$C_4$ alcohols, or of acrylates or methacrylates of $C_8$–$C_{30}$ alcohols,
   (C) a sequential or grafted block copolymer, or mixture thereof comprising at least one block resulting from the polymerization of dienes, which is optionally hydrogenated, and at least one block of at least one polymer wherein said at least one polymer is a vinyl or acrylic polymer, polyether, polyester, or a mixture thereof.

22. A method according to claim 21, wherein said at least one polymer is a non-film-forming polymer.

* * * * *